US00PP25836P2

(12) United States Plant Patent
Wood

(10) Patent No.: US PP25,836 P2
(45) Date of Patent: Aug. 25, 2015

(54) ***HYDRANGEA* PLANT NAMED 'SMHMES14'**

(50) Latin Name: *Hydrangea macrophylla*
Varietal Denomination: SMHMES14

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 132 days.

(21) Appl. No.: 13/987,987

(22) Filed: Sep. 20, 2013

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Anne Grunberg
(74) *Attorney, Agent, or Firm* — C. A. Whealy

(57) ABSTRACT

A new and distinct cultivar of *Hydrangea* plant named 'SMHMES14', characterized by its upright, outwardly spreading and mounded plant habit; strong and sturdy dark brown-colored stems; early flowering habit; large mophead-type inflorescences with large sterile flowers; sterile flowers dark pink or blue in color depending on aluminum sulfate treatments; and good winter hardiness.

4 Drawing Sheets

Botanical designation: *Hydrangea macrophylla.*
Cultivar denomination: 'SMHMES14'.

BACKGROUND OF THE INVENTION

The present invention relates to a new and distinct *Hydrangea* plant, botanically known as *Hydrangea macrophylla* and hereinafter referred to by the name 'SMHMES14'.

The new *Hydrangea* plant is a product of a planned breeding program conducted by the Inventor in Grand Haven, Mich. The objective of the breeding program was to develop new *Hydrangea* plants with reblooming habit, strong stems and attractive inflorescences.

The new *Hydrangea* plant originated from an open-pollination during the summer of 2003 of *Hydrangea macrophylla* 'Bailmer', disclosed in U.S. Plant Pat. No. 15,298, as the female, or seed parent with an unknown selection of *Hydrangea macrophylla* as the male, or pollen, parent. The new *Hydrangea* plant was discovered and selected by the Inventor as a single flowering plant from within the progeny of the stated open-pollination in a controlled environment in Grand Haven, Mich. in May, 2005.

Asexual reproduction of the new *Hydrangea* plant by softwood cuttings in a controlled environment in Grand Haven, Mich. since June, 2005 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHMES14'. These characteristics in combination distinguish 'SMHMES14' as a new and distinct *Hydrangea* plant:

1. Upright, outwardly spreading and mounded plant habit.
2. Strong and sturdy dark brown-colored stems.
3. Early flowering habit.
4. Large mophead-type inflorescences with large sterile flowers.
5. Sterile flowers dark pink or blue in color depending on aluminum sulfate treatments.
6. Good winter hardiness.

Plants of the new *Hydrangea* differ from plants of the female parent, 'Bailmer', in the following characteristics:

1. Plants of the new *Hydrangea* have stronger, sturdier and darker-colored stems than plants of 'Bailmer'.
2. Sepals of sterile flowers of plants of the new *Hydrangea* have acute apices whereas sepals of sterile flowers of 'Bailmer' have obtuse apices.
3. Sepal color of sterile flowers of the new *Hydrangea* is more intense and richer than sepal color of sterile flowers of 'Bailmer'.
4. Plants of the new *Hydrangea* are more winter hardy than plants of 'Bailmer'.

Plants of the new *Hydrangea* can be compared to plants of *Hydrangea macrophylla* 'Nikko Blue', not patented. In side-by-side comparisons, plants of the new *Hydrangea* differed primarily from plants of 'Nikko Blue' in the following characteristics:

1. Plants of the new *Hydrangea* flowered about three to four weeks earlier than plants of 'Nikko Blue'.
2. Sepals of sterile flowers of plants of the new *Hydrangea* had acute apices whereas sepals of sterile flowers of 'Nikko Blue' had obtuse apices.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a top perspective view of a typical flowering plant of 'SMHMES14' grown without aluminum sulfate treatments.

The photograph on the second sheet is a close-up view of typical inflorescences of 'SMHMES14' grown without aluminum sulfate treatments.

The photograph on the third sheet comprises a top perspective view of a typical flowering plant of 'SMHMES14' grown with aluminum sulfate treatments.

The photograph on the fourth sheet is a close-up view of typical inflorescences of 'SMHMES14' grown with aluminum sulfate treatments.

DETAILED BOTANICAL DESCRIPTION

Plants used for the aforementioned photographs and the following description were grown during the summer in three-gallon containers in an outdoor shadehouse in Grand Haven, Mich. and under cultural practices typical of commercial *Hydrangea* production. Plants of the new *Hydrangea* were three years old when the photographs and description were taken. In the following description, color references are made to The Royal Horticultural Society Colour Chart, 1995 Edition, except where general terms of ordinary dictionary significance are used.

Botanical description: *Hydrangea macrophylla* 'SMHMES14'.

Parentage:

*Female, or seed, parent.*—*Hydrangea macrophylla* 'Bailmer', disclosed in U.S. Plant Pat. No. 15,298.

*Male, or pollen, parent.*—Unknown selection of *Hydrangea macrophylla*, not patented.

Propagation:

*Type cutting.*—By softwood cuttings.

*Time to initiate roots, summer.*—About ten days at temperatures about 24° C.

*Time to produce a rooted young plant, summer.*—About 40 days at temperatures about 24° C.

*Root description.*—Fine and thick, fibrous; white and brown in color.

*Rooting habit.*—Freely branching; dense.

Plant description:

*Plant form and growth habit.*—Perennial deciduous shrub; upright, outwardly spreading and mounded plant habit; inverted triangle; strong and sturdy lateral branches; freely branching habit with about nine lateral branches developing per plant; vigorous growth habit.

*Plant height.*—About 39 cm.

*Plant diameter or area of spread.*—About 58 cm.

*Lateral branches.*—Length: About 25 cm. Diameter: About 5 mm. Internode length: About 4.5 cm. Texture: Smooth, glabrous. Strength: Strong, sturdy. Color, young: Close to 144C. Color, mature: Close to 165A.

Leaf description:

*Arrangement.*—Opposite, simple.

*Length.*—About 9.5 cm.

*Width.*—About 5.5 cm.

*Shape.*—Ovate.

*Apex.*—Acuminate.

*Base.*—Obtuse.

*Margin.*—Serrulate.

*Texture, upper surface.*—Smooth, glabrous.

*Texture, lower surface.*—Coarse, pubescent.

*Venation pattern.*—Pinnate.

*Color.*—Developing leaves, upper surface: Close to 144A. Developing leaves, lower surface: Close to 138B. Fully expanded leaves, upper surface: Close to 137A; venation, close to 147A. Fully expanded leaves, lower surface: Close to 137D; venation, close to 146B.

*Petioles.*—Length: About 3.5 cm. Diameter: About 4 mm. Texture, upper and lower surfaces: Smooth, glabrous. Color, upper and lower surfaces: Close to 144A.

Flower description:

*Flower type and habit.*—Single sterile and fertile flowers arranged on large terminal mophead-type cymes that are roughly spherical; flowers face upright or outwardly.

*Fragrance.*—None detected.

*Natural flowering season.*—Early flowering habit; plants flower throughout the summer in Grand Haven, Mich.; flowers not persistent.

*Quantity of flowers.*—Freely flowering habit; about 14 fertile flowers and about 935 sterile flowers per inflorescence.

*Inflorescence height.*—About 8 cm.

*Inflorescence diameter.*—About 12.5 cm.

*Flower diameter, fertile flowers.*—About 7 mm.

*Flower depth (height), fertile flowers.*—About 5 mm.

*Flower diameter, sterile flowers.*—About 3.3 cm.

*Flower depth (height), sterile flowers.*—About 3 mm.

*Flower buds, fertile flowers.*—Length: About 5 mm. Diameter: About 3 mm. Shape: Obovate. Color: Close to 145C.

*Flower buds, sterile flowers.*—Length: About 7 mm. Diameter: About 4 mm. Shape: Obovate. Color: Close to 160D.

*Petals, fertile flowers only.*—Quantity per flower and arrangement: Five in a single whorl. Length: About 4 mm. Width: About 2 mm. Shape: Elliptic. Apex: Acute. Base: Cuneate. Margin: Entire. Texture, upper and lower surfaces: Smooth, glabrous. Color, without aluminum sulfate: When opening, upper and lower surfaces: Close to 66C. Fully opened, upper and lower surfaces: Close to 66D. Color, with aluminum sulfate: When opening, upper and lower surfaces: Close to 95D. Fully opened, upper and lower surfaces: Close to 95D.

*Sepals, fertile flowers.*—Quantity per flower and arrangement: Seven in a single whorl. Length: About 1 mm. Width: About 1 mm. Shape: Subulate. Apex: Acute. Base: Cuneate. Margin: Entire. Texture, upper and lower surfaces: Smooth, glabrous. Color: When opening, upper and lower surfaces: Close to 60D. Fully opened, upper and lower surfaces: Close to 64D.

*Sepals, sterile flowers.*—Quantity per flower and arrangement: Four in a single whorl. Length: About 1.7 cm. Width: About 1.5 cm. Shape: Ovate. Apex: Acute. Base: Obtuse. Margin: Entire. Texture, upper and lower surfaces: Smooth, glabrous. Color, without aluminum sulfate: When opening, upper surface: Close to 154D becoming closer to 66D. When opening, lower surface: Close to 66D. Fully opened, upper and lower surfaces: Close to 66D and 58D. Color, with aluminum sulfate: When opening, upper surface: Close to 154D becoming closer to 95C. When opening, lower surface: Close to 95C to 95D. Fully opened, upper and lower surfaces: Close to 95C to 95D.

*Pedicels, fertile flowers*.—Angle: About 30° to 50° from inflorescence axis. Strength: Strong, sturdy. Length: About 6 mm. Diameter: About 1 mm. Texture: Pubescent. Color: Close to 63C.

*Pedicels, sterile flowers*.—Angle: About 50° to 70° from inflorescence axis. Strength: Strong, sturdy. Length: About 1.3 cm. Diameter: About 1 mm. Texture: Pubescent. Color: Close to 63C.

*Reproductive organs, fertile flowers*.—Stamens: Quantity per flower: About nine. Filament length: About 3 mm. Filament color: Close to 155D. Anther shape: Round. Anther length: About 1 mm. Anther color: Close to 4D. Pollen amount: Scarce. Pollen color: Close to 4D. Pistils: Pistil quantity per flower: About three. Pistil length: About 4 mm. Stigma shape: Round. Stigma color: Close to 155B. Style length: About 2 mm. Style color: Close to 66B. Ovary color: Close to 150D.

*Reproductive organs, sterile flowers*.—Stamens: Quantity per flower: About six. Filament length: About 1 mm. Filament color: Close to 62D. Anther shape: Round. Anther length: About 0.5 mm. Anther color: Close to 155C. Pollen amount: None observed. Pistils: Pistil quantity per flower: About two. Pistil length: About 1 mm. Stigma shape: Round. Stigma color: Close to 84D. Style length: About 0.5 mm. Style color: Close to 57B.

*Seeds, fertile flowers only*.—Quantity per inflorescence: Numerous. Size: Less than 0.1 mm by less than 0.1 mm; dust-like. Color: Brown.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures ranging from about −27° C. to about 37° C.

It is claimed:

1. A new and distinct *Hydrangea* plant named 'SMHMES14' as illustrated and described.

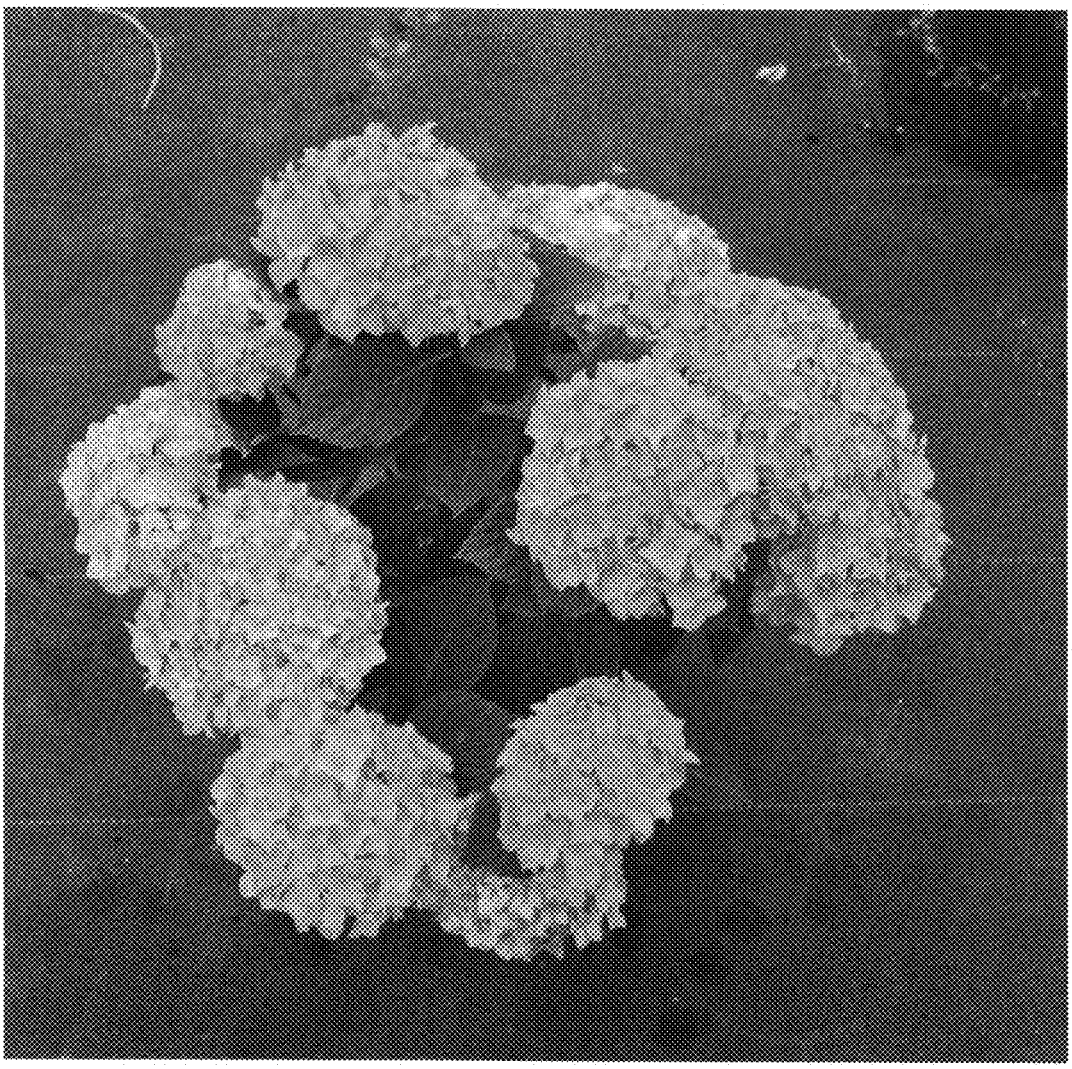

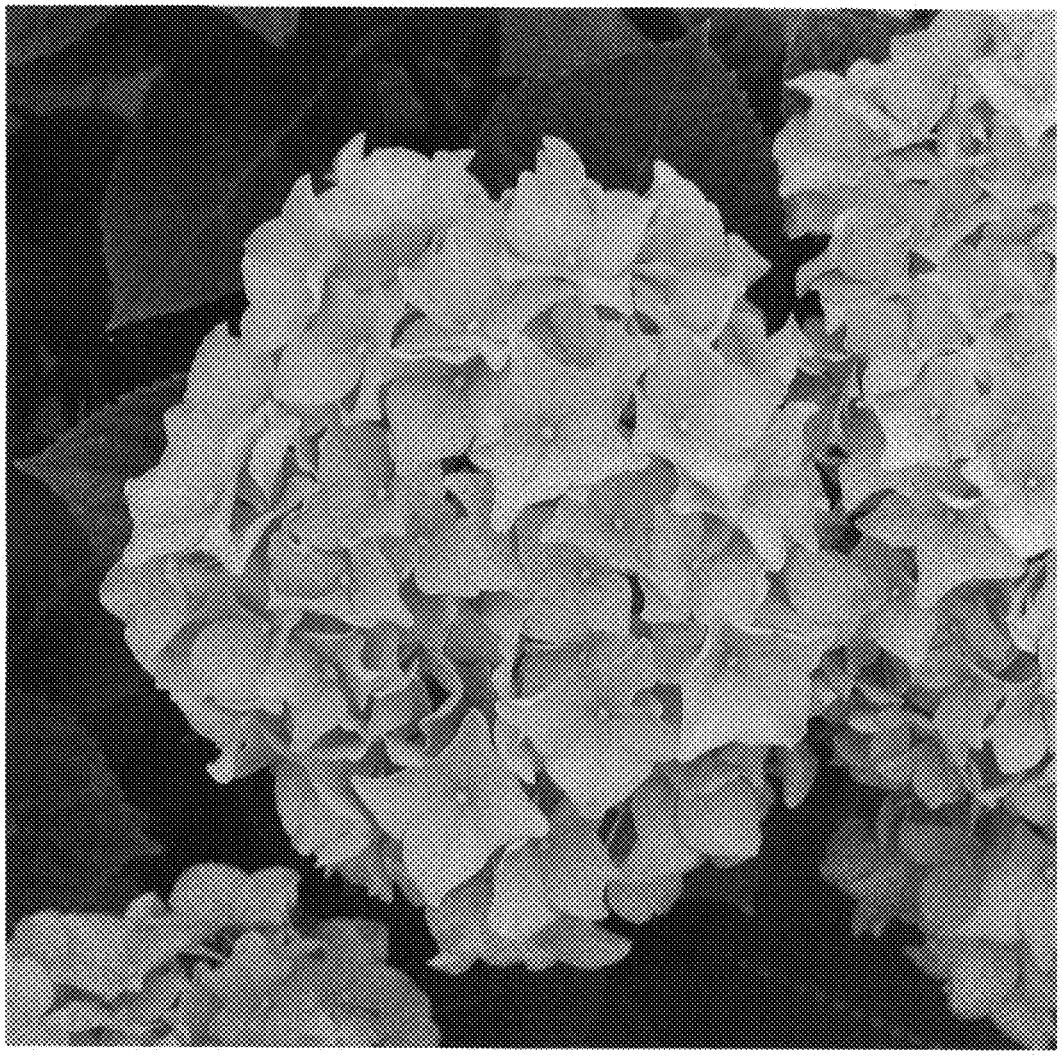

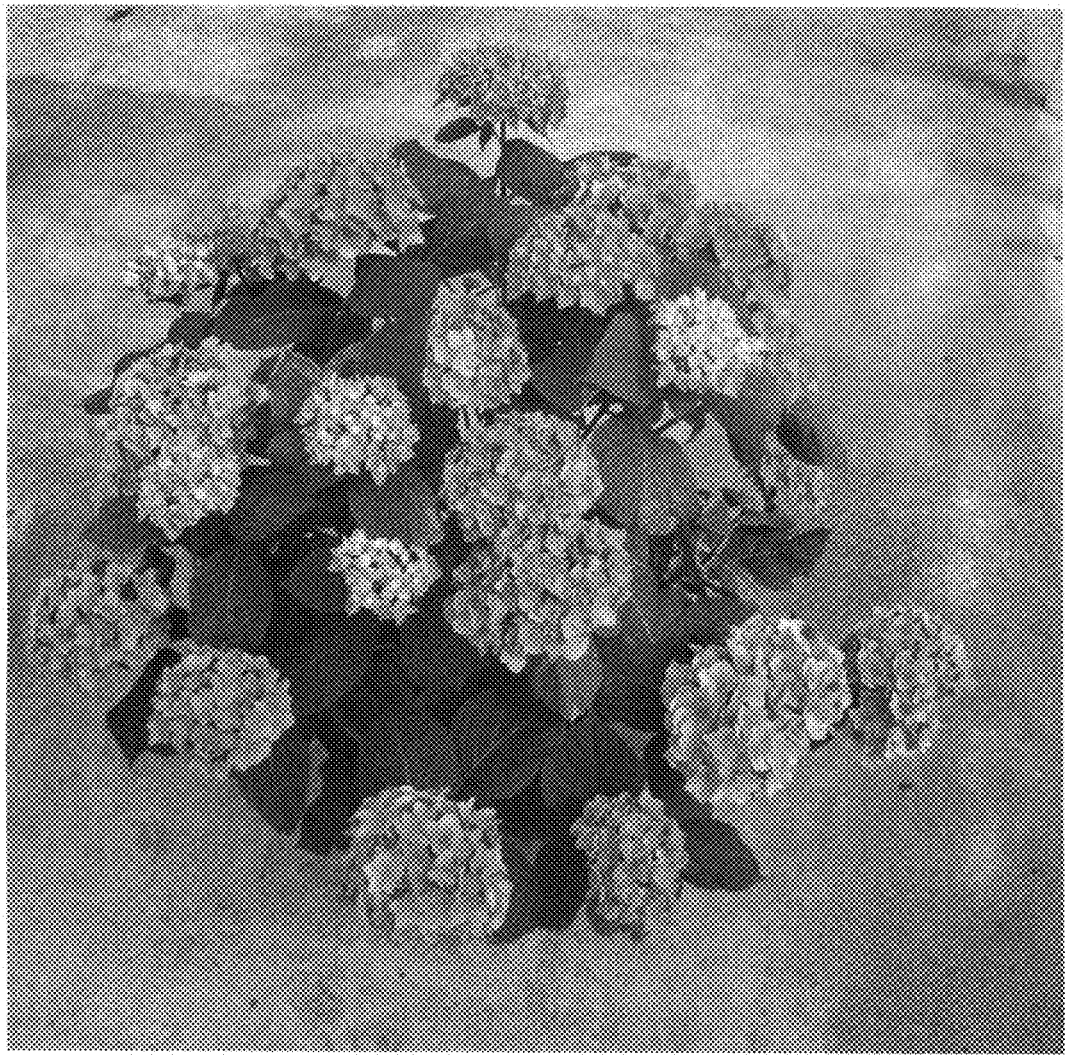

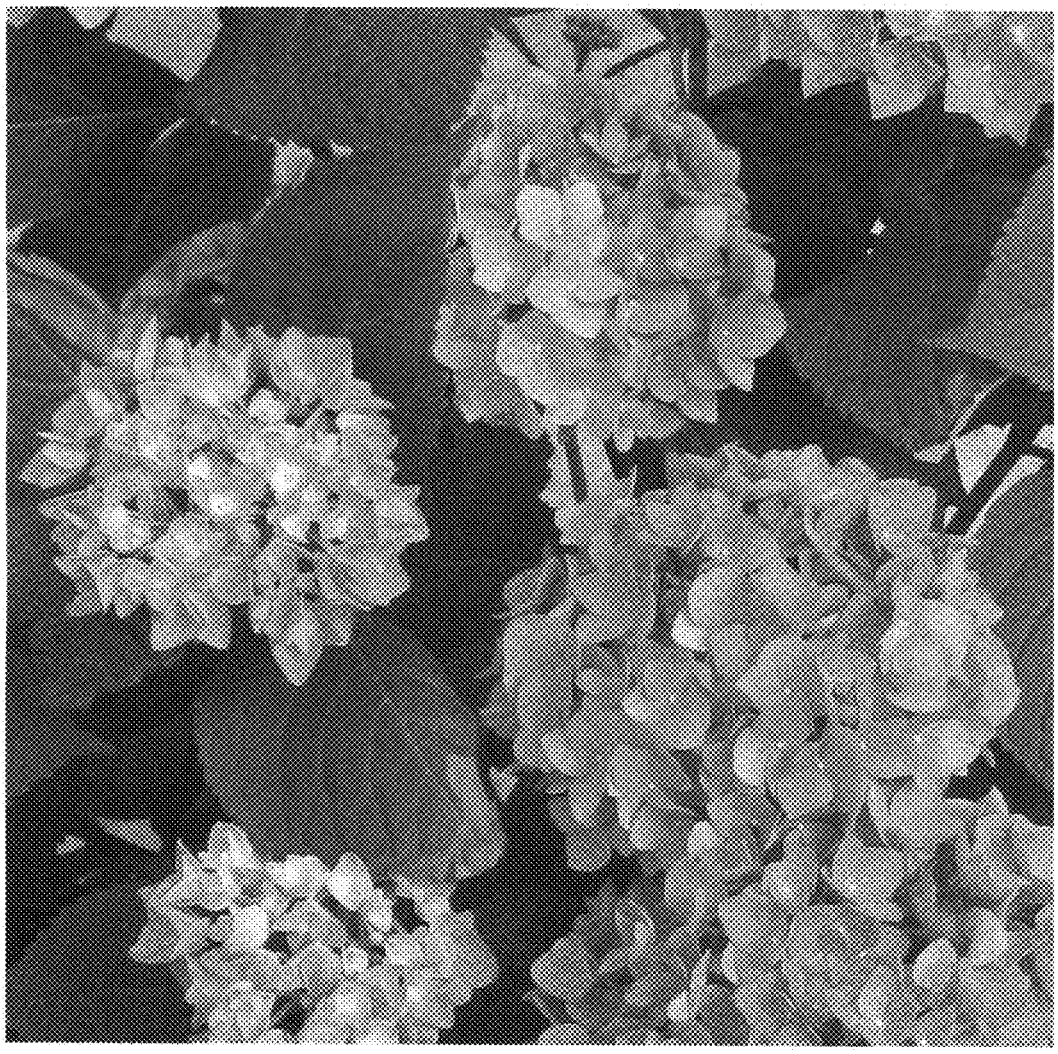

* * * * *